United States Patent [19]

Hamada et al.

[11] Patent Number: 4,469,894

[45] Date of Patent: Sep. 4, 1984

[54] PROCESS FOR PREPARATION OF HYDROXYBENZALDEHYDES

[75] Inventors: Kazuhiko Hamada; Gohfu Suzukamo, both of Osaka, Japan

[73] Assignee: Sumitomo Chemical Co., Ltd., Osaka, Japan

[21] Appl. No.: 388,817

[22] Filed: Jun. 16, 1982

[30] Foreign Application Priority Data

Jun. 16, 1981 [JP] Japan ................................ 56-93314

[51] Int. Cl.³ ............................................. C07C 45/45
[52] U.S. Cl. ............................................. 568/437
[58] Field of Search ....................................... 568/437

[56] References Cited

U.S. PATENT DOCUMENTS 3,365,500  1/1968  Pontz ................................. 568/437

OTHER PUBLICATIONS

Sasson et al., Tetrahedron Letters, No. 39, (1979), 3753-3756.
Hine et al., Jour. Amer. Chem. Soc., vol. 81, (1959), 6446-6449.
Yonovich et al., Tetrahedron Letters, vol. 21, (1980), 1875-1876.
Casiraghi et al., J. C. S. Perkin I (1980), 1862-1865.

Primary Examiner—Bernard Helfin
Attorney, Agent, or Firm—Sughrue, Mion, Zinn, Macpeak & Seas

[57] ABSTRACT

In a Reimer-Tiemann reaction for the preparation of a mixture of salicylaldehyde and p-hydroxybenzaldehyde, improved yield of the product and high selectivity of salicylaldehyde can be obtained when an alkali metal salt of a phenol is reacted with a reaction mixture comprised of chloroform and a slurry of an alkali metal hydroxide (preferably, in a fine powder state thereof) and an inert organic solvent and optionally, a catalytic amount of a surfactant.

4 Claims, No Drawings

PROCESS FOR PREPARATION OF HYDROXYBENZALDEHYDES

FIELD OF THE INVENTION

The present invention relates to an improved process for the preparation of hydroxybenzaldehydes, particularly, salicylaldehyde, comprising reacting an alkali metal salt of phenol with a new reaction mixture comprised of chloroform and a fine powder of an alkali metal hydroxide in an inert organic solvent in a slurry state.

BACKGROUND OF THE INVENTION

Salicylaldehyde is an industrially important compound as an intermediate chemical for the preparation of perfumes, pesticides, chelating agents, etc.

The following methods are, for example, hitherto known as the preparation of hydroxybenzaldehyde:

(1) So-called Reimer-Tiemann Reaction:

In accordance with this reaction, a phenol is reacted with chloroform and an aqueous alkali solution in a heterogeneous system to prepare a mixture of salicylaldehyde and p-hydroxybenzaldehyde. Generally, in this method, the yield of salicylaldehyde is low. Further, an excess amount of chloroform over the phenol is necessary, and recovery and recycling of unreacted chloroform and phenol are not necessarily easy (and expensive).

There is also known a Dow method as one of the typical examples of improved Reimer-Tiemann reaction method, wherein a phenol, chloroform and an alkali metal hydroxide are reacted in a solvent medium consisting of aqueous methanol containing 10 to 75% by weight of methanol (as disclosed in U.S. Pat. No. 3,365,500). Even in this method, the conversion of the phenol is, however, low, and the separation and recovery of unreacted phenol are difficult. Further, the production ratio of salicylaldehyde and p-hydroxybenzaldehyde is lower than that obtained under the ordinary Reimer-Tiemann condition. Therefore, this Dow method accompanies difficulties in the separation of the components from the reaction mixture.

(2) Method proposed by Yoel Sasson et al. [*Tetrahedron Lett.*, 3753 (1979) and 1875 (1980)]:

In accordance with this method, when an aliphatic tertiary amine is added to the reaction mixture obtained under the ordinary Reimer-Tiemann condition (where excess amounts of chloroform and an aqueous alkali solution are used over the phenol), the yield of salicylaldehyde is improved without any undesirable influence over the yield of p-hydroxybenzladehyde. But this method accompanies not a few disadvantages. Namely, the tertiary amine which can be used is limited to a few species such as $(n-C_4H_9)_3N$, etc., and a reaction to form an alkyl ether of phenol also takes place competitively. Further, excess amounts of chloroform and an aqueous alkali solution over the phenol need be used, which leads to the foregoing disadvantages. Still further, it has been experimentally confirmed by the present inventors under the same conditions as reported that the effects brought by the addition of the aliphatic tertiary amine are not so drastic as reported.

(3) A method in which a salicylaldehyde is prepared in good yield by one step reaction using as starting materials a phenol and a formaldehyde and a specific catalyst (a base represented by a tertiary amine and/or an organometallic salt):

This method is described in, for example, Japanese Patent Application (OPI) Nos. 34737/78 and 163538/79 (the term "OPI" as used herein refers to a "published unexamined Japanese patent application") and *J.C.S.*, Perkin I, 1862 (1980) and the like. This method, however, accompanies not a few disadvantages. In other words, an excess amount of formaldehyde over the phenol, a poisonous catalyst (e.g., $SnCl_2$, $SnCl_4$, $Cr(acac)_3$, etc.) or a fairly large amount of an organic amine as an additive need be used, and therefore, a complicated post-treatment and waste water treatment and the like are inevitable.

SUMMARY OF THE INVENTION

In order to solve the drawbacks of the prior art methods, the present inventors have intensively studied to provide a new method for selectively preparing a hydroxybenzaldehyde, paticularly, salicylaldehyde, without using excess amounts of chloroform and an alkali over the phenol, poisonous catalysts (such as organometallic salts) or other additives, whereby post-treatment such as separation, a recovery operation, etc., can be eliminated. It has been found that hydroxybenzaldehydes (mainly, salicylaldehyde) can be prepared with good yield and high selectivity when an alkali metal salt of a phenol (which can be easily prepared in advance) is reacted with a reaction mixture comprised of chloroform and a fine powder of an alkali metal hydroxide in an anhydrous or substantially anhydrous reaction medium which comprises an inert organic solvent and optionally, a catalytic amount of surfactant in a slurry state. It has also been found that only a specific hydroxybenzaldehyde can be prepared selectively without decomposition of the other hydroxybenzaldehyde in a reaction system where the reaction is initiated under an anhydrous or substantially anhydrous condition. These findings have led to the present invention.

It is generally admitted that an excess amount of an aqueous alkali solution over the phenol should be used in the traditional Reimer-Tiemann reaction. In contrast, in accordance with the process of the present invention, an alkali phenolate is reacted with chloroform under heating in a slurry of a fine powder of an alkali metal hydroxide individually prepared in advance under an anhydrous or substantially anhydrous condition, and such process is a quite new process in carrying out the Reimer-Tiemann reaction. Consequently, it is quite unexpected that salicylaldehyde can be prepared with good yield and high selectivity under the conditions specified in the present invention.

A primary object of the present invention is, therefore, to eliminate the above-described drawbacks of the prior art methods and to provide a new process for the selective preparation of hydroxybenzaldehydes.

Another object of the present invention is to provide an improved process for the selective preparation of hydroxybenzaldehydes, particularly, salicylaldehyde.

A further object of the present invention is to provide an improved process for reacting an alkali metal salt of a phenol (an alkali phenolate) with a reaction mixture comprised of chloroform and a fine powder of an alkali metal hydroxide, whereby hydroxybenzaldehydes, particularly, salicylaldehyde, can be obtained with high selectivity and good yield and with less amounts of by-products formed.

These and other objects and advantages of the present invention will be apparent to one skilled in the art from the following description.

DETAILED DESCRIPTION OF THE INVENTION

Examples of alkali phenolates as a starting material which can be used in the present invention are lithium phenolate, sodium phenolate, potassium phenolate, cesium phenolate, etc. Of these compounds, sodium phenolate and potassium phenolate are preferable because these materials are inexpensively available.

The alkali phenolates which are used as the starting material can be, for example, prepared by the following methods. In one method, after dissolving phenol in dried toluene, an equimolar amount of an alkali metal (e.g., commercially available metallic sodium, metallic potassium, etc.) is added to the mixture, and the resulting mixture is heated, followed by concentrating a toluene solution containing the alkali metal phenolate and then drying it under reduced pressure (see *Organic Synthesis, Coll.*, Vol. 1, 58, etc.). In another method, an aqueous solution of 50 wt% sodium hydroxide is added to phenol, and the mixture is stirred and heated. Water present in the reaction system is then removed, and the residue is concentrated and dried under reduced pressure. In the latter method, the water content of the alkali metal phenolate used as the starting material should be less than 3 to 5 wt%.

Fine powdery alkali metal hydroxide/organic solvent slurries which can be used in the present invention are those prepared in the following method. Namely, an alkali metal hydroxide (e.g., sodium hydroxide, potassium hydroxide, lithium hydroxide, etc.) is added to an organic solvent which is inert to the reaction, and the mixture is intensely shaken in a wet phase, to thereby obtain an about 30 to 60 mesh size fine powdery alkali metal hydroxide/organic slurry. Examples of organic solvents which are inert to the reaction are aromatic hydrocarbons (e.g., benzene, toluene, xylene, etc.), ethers (e.g., anisol, dibutyl ether, diisopropyl ether, etc.), esters (e.g., ethyl acetate, methyl acetate, etc.), aliphatic alcohols (e.g., methanol, ethanol, butanol, ethylene glycol, etc.) and the like. It is possible to control the selectivity of the product to some extent by selecting the organic solvent used. Of these slurries, a slurry comprising a fine powder of sodium hydroxide or potassium hydroxide and an aromatic hydrocarbon such as benzene, toluene, etc., are preferred.

A typical embodiment of the present invention is explained as follows:

Pellets of sodium hydroxide having a purity higher than 95 wt% and some definite excess amount of dried benzene or toluene over the former are charged in a vessel made of polyethylene. Alumina balls (internal diameter: about 5 mm to 10 mm, number of balls: 10 to 15) are added thereto, then the system is shielded, fastened firmly and shaken intensely in a wet phase by means of a paint shaker, etc., for 30 minutes to 1 hour, to thereby obtain a desired slurry. When pellet-type potassium hydroxide having a purity higher than 85 wt% is used, it is preliminarily molten by heating and dehydrated by drying under reduced pressure to prepare solid-type potassium hydroxide. Some definite excess amount of a dried organic solvent over the potassium hydroxide is added thereto, and the mixture is shaken intensely in a wet phase in the same manner as in the case of sodium hydroxide above, to obtain a slurry.

The alkali concentration of the thus-obtained slurry is determined from the relation between the amount of the anhydrous state alkali hydroxide used and the amount of the excess amount of organic solvent used. As chloroform which can be used, normal grade reagent can be used without any pretreatment.

In the reaction system of the present invention, a surfactant which is used in a catalytic amount improves the conversion of phenol and the formation ratio of salicylaldehyde/p-hydroxybenzaldehyde. But, the use of the surfactant is not essential, and the reaction may proceed without using it. Examples of surfactants which can be used in the present invention are nonionic surfactants, cationic surfactants, anionic surfactants and amphoteric surfactants. They can be used alone or in combination. A preferable amount of the surfactant used in the reaction is from 0.1 to 5.0 mol% of the alkali phenolate.

Specific examples of nonionic surfactants used in the present invention are polyethylene glycol-based surfactants (e.g., higher alcohol ethyleneoxide addition compounds, phenol ethyleneoxide addition compounds, fatty acid ethyleneoxide addition compounds, etc.), polyhydric alcohol-based surfactants (e.g., higher fatty acid sorbitan esters, sugar esters, etc.) and the like. Specific examples of cationic surfactants used in the present invention are quaternary ammonium salt-based surfactants (e.g., cetyl trimethylammonium chloride, tetrabutylammonium hydroxide, etc.), quaternary phosphonium salt-based surfactants, pyridinium salt-based surfactants and the like. Specific examples of anionic surfactants used in the present invention are alkali metal salts of higher fatty acids, higher alkyl sulphonic acid salts, sulfuric ester salts of higher alcohols and the like. Specific examples of amphoteric surfactants used in the present invention are amino acid-based surfactants, betaine-based surfactants and the like. Of these, the nonionic surfactants are preferred. The use of, for example, Tween 80, Span 85, etc., enables one to proceed the reaction smoothly.

As for the proportion of the reactants charged in the reaction system, there are employable many alternatives within a range of from the ordinary laboratory condition wherein a large excess amount of an alkali and chloroform is employed to not more than the estimated theoretical amount thereof (i.e., phenol/alkali/chloroform=1.0/4.0/1.0). Generally, the reactants are used in a range of phenol/alkali/chloroform of from 1.0/10.0/10.0 to 1.0/2.0/0.3.

The reaction according to the present invention can be carried out in the following manner. Namely, predetermined amounts of an alkali phenolate, a slurry of a fine powder of an alkali metal hydroxide and an inert organic solvent and optionally, a surfactant are charged in a reactor equipped with a condenser, and a predetermined amount of chloroform is added to the stirred mixture under heating (generally, at a temperature of from 50° C. to 100° C.), whereby the reaction is proceeded. The reaction substantially completes within 30 minutes to 10 hours. After completion of the reaction, the reaction mixture is cooled to room temperature (e.g., about 15° to 30° C.), and a predetermined amount of ethyl acetate (or methyl isobutyl ketone) is added thereto. Thereafter, an excess amount of concentrated hydrochloric acid (12 to 34 wt%) is added to the resulting mixture under cooling and stirring to adjust the pH of the aqueous layer to 1 to 2. After the separation of the organic layer, the aqueous layer is extracted twice with ethyl acetate, and the extracts are collected together. Analysis of the product is carried out by analyzing the organic layer by a usual method such as gas chromatography (internal standard method) and so on.

The present invention is explained in more detail with reference to the following Examples, but it is not to be construed that the present invention is limited thereto.

EXAMPLE 1

A three-necked flask equipped with a condenser and a stirrer was charged with 3.0 g (0.0259 mol) of sodium phenolate and 20.66 g of an anhydrous sodium hydroxide/benzene slurry [sodium hydroxide 5.16 g (0.129 mol)/benzene 15.5 g], each of which was individually prepared in advance, and 0.15 g (about 0.00014 mol) of Tween 80. The mixture was heated to 60° to 65° C. with stirring. When the temperature of the reaction system became constant, 18.5 g (0.155 mol) of chloroform charged in the side inlet tube was carefully added dropwise to the stirred mixture over 30 minutes to 1 hour. After the completion of dropwise addition, the reaction temperature was elevated to 75° to 80° C., followed by stirring for an additional about 3 hours. The initiation of the reaction could be visually observed by the change of color of the emulsion to yellowish brown as the dropwise addition of chloroform initiated. After the completion of reaction, the reaction mixture was cooled to room temperature (i.e., about 15° to 30° C.), and 10 ml of ethyl acetate (or methyl isobutyl ketone) was added thereto. Thereafter, concentrated hydrochloric acid (12 wt%) in an amount of 2 to 3 times the stoichiometric amount was added to the reaction mixture under cooling to 0° to 5° C., and the resulting mixture was stirred to adjust the pH of the aqueous layer to 1 to 2. After the separation of the ethyl acetate layer, the aqueous layer was thoroughly extracted twice with ethyl acetate (10 ml×2). These extracts were collected together, and then subjected to quantitative analysis by gas chromatography. The result it was found to be a conversion based on sodium phenolate used of the phenol of 95.7% and a yield based on phenol consumed of hydroxybenzaldehydes (salicylaldehyde plus p-hydroxybenzaldehyde) of 62.8%, respectively. The proportion of salicylaldehyde to p-hydroxybenzaldehyde formed was 7.8:1.

EXAMPLES 2 TO 11

The reaction was carried out in the same manner as in Example 1. The results obtained are shown in Table 1 below. In Table 1, SAL and POBA mean salicylaldehyde and p-hydroxybenzaldehyde, respectively.

TABLE 1

| Example No. | Reactant Base | Anhydrous Alkali/Organic Solvent Slurry | Chloroform (to be added dropwise) | Proportion of PhOH/MOH/CHCl₃ Charged | Surfactant (mol % of alkali phenolate) | Reaction Condition Temperature (°C.) | Time (hr) | Conversion of Phenol (%) | Yield of SAL + POBA (based on phenol consumed) (%) | SAL/POBA |
|---|---|---|---|---|---|---|---|---|---|---|
| 2 | PhONa (3.0 g) | NaOH/Ph | CHCl₃ | 0.17/1.0/1.0 | Nil | 75-80 | 5.0 | 65.0 | 30.0 | 5.7 |
| 3 | " | NaOH/PhMe | " | " | Tween 80 (0.54) | 80-85 | 4.5 | 88.9 | 60.1 | 6.9 |
| 4 | " | NaOH/Bu₂O | " | " | Tween 80 (0.54) | " | " | 80.3 | 59.3 | 6.6 |
| 5 | PhOK (3.0 g) | KOH/Ph | " | " | Tween 80 (0.54) | 75-80 | " | 70.8 | 46.5 | 4.5 |
| 6 | PhONa (3.0 g) | NaOH/Ph | " | " | Span 85 (0.50) | " | " | 82.7 | 53.7 | 5.13 |
| 7 | " | " | " | " | C₁₂H₂₅NMe₃Cl (1.0) | " | " | 92.1 | 61.0 | 7.4 |
| 8 | " | " | " | " | Tween 80 (0.70) | 85-90 | 5.5 | 75.7 | 53.9 | 8.4 |
| 9 | PhOLi (3.0 g) | LiOH/Ph | " | 3.0/6.0/1.0 | Tween 80 (0.50) | 60-65 | 6.5 | 34.2 | 58.0 | 5.2 |
| 10 | PhONa (3.0 g) | NaOH/Ph | " | 1.5/5.4/1.0 | Tween 80 (0.50) | 75-80 | 5.0 | 48.9 | 61.3 | 7.0 |
| 11 | PhOK (3.0 g) | KOH/HOCH₂CH₂OH | " | 0.17/1.0/1.0 | Nil | 80-85 | 4.5 | 39.7 | 73.1 | 0.77 |

What is claimed is:

1. In a process for the preparation of a mixture of salicylaldehyde and p-hydroxybenzaldehyde by the reaction of a phenol and an alkali metal hydroxide in a heterogeneous system by a Reimer-Tiemann reaction, the improvement which comprises reacting an alkali metal salt of a phenol with a reaction mixture comprised of chloroform, a slurry of alkali metal hydroxide, a surfactant and an inert organic solvent under an anhydrous reaction condition or a substantially anhydrous reaction condition wherein said reacting is carried out at a temperature of from 50° C. to 100° C., the ratio of phenol/alkali/chloroform is from 1.0/10.0/10.0 to 1.0/2.0/0.3 and the surfactant is present in an amount of from 0.1 to 5.0 mol % of the alkali metal salt of the phenol.

2. A process of claim 1, wherein said alkali metal hydroxide is in a state of fine powder of about 30 to 60 mesh size.

3. A process of claim 1 or 2, wherein said alkali metal hydroxide is sodium hydroxide or potassium hydroxide, or a combination thereof.

4. A process for the preparation of salicylaldehyde and p-hydroxybenzaldehyde which comprises reacting (a) an alkali salt of a phenol with (b) a reaction mixture comprised of chloroform and a slurry of alkali metal hydroxide powder, a surfactant and an inert organic solvent, under anhydrous or substantially anhydrous reaction conditions at a temperature of from 50° to 100° C., a ratio of phenol/alkali/chloroform of from 1.0/10.0/10.0 to 1.0/2.0/0.3 and a surfactant amount of from 0.1 to 5.0 mol % of the alkali metal salt of the phenol.

* * * * *